US008697124B2

(12) United States Patent
Persicaner et al.

(10) Patent No.: US 8,697,124 B2
(45) Date of Patent: Apr. 15, 2014

(54) SOLID DOSAGE FORM OF COATED BISPHOSPHONATE PARTICLES

(75) Inventors: Peter Persicaner, Vic (AU); Craig Judy, Vic (AU)

(73) Assignee: Arrow International Limited, Valetta, MT (US)

( * ) Notice: Subject to any disclaimer, the term of this patent is extended or adjusted under 35 U.S.C. 154(b) by 682 days.

(21) Appl. No.: 12/310,388

(22) PCT Filed: Aug. 24, 2007

(86) PCT No.: PCT/GB2007/003224
§ 371 (c)(1),
(2), (4) Date: Feb. 24, 2009

(87) PCT Pub. No.: WO2008/023184
PCT Pub. Date: Feb. 28, 2008

(65) Prior Publication Data
US 2009/0317460 A1 Dec. 24, 2009

(30) Foreign Application Priority Data
Aug. 24, 2006 (GB) .................................. 0616794.4

(51) Int. Cl.
*A61K 31/663* (2006.01)
*A61K 31/675* (2006.01)
*A61K 9/16* (2006.01)
*A61K 9/20* (2006.01)
*A61K 9/50* (2006.01)
*C07F 9/38* (2006.01)
*A61J 3/10* (2006.01)

(52) U.S. Cl.
CPC ............ *A61K 31/663* (2013.01); *A61K 31/675* (2013.01); *A61K 9/2077* (2013.01); *A61K 9/501* (2013.01); *A61K 9/5015* (2013.01); *A61K 9/5026* (2013.01); *A61K 9/5031* (2013.01); *C07F 9/3865* (2013.01); *A61J 3/10* (2013.01)
USPC ............. 424/464; 424/465; 514/89; 514/102; 514/108

(58) Field of Classification Search
CPC ... A61K 9/501; A61K 31/675; A61K 31/663; A61J 3/10; C07F 9/3865
See application file for complete search history.

(56) References Cited

U.S. PATENT DOCUMENTS

| | | | |
|---|---|---|---|
| 5,776,499 A * | 7/1998 | Pohjala et al. ................ | 424/489 |
| 6,143,326 A | 11/2000 | Möckel et al. | |
| 6,350,471 B1 | 2/2002 | Seth | |
| 6,676,965 B1 | 1/2004 | Lulla et al. | |
| 6,781,011 B2 * | 8/2004 | Montchamp et al. ........... | 562/13 |
| 2002/0187184 A1 | 12/2002 | Golomb et al. | |
| 2003/0013686 A1 | 1/2003 | Golomb et al. | |
| 2003/0032628 A1 | 2/2003 | Katdare et al. | |
| 2003/0175355 A1 | 9/2003 | Tobyn et al. | |
| 2004/0121007 A1 | 6/2004 | Kaestle et al. | |
| 2004/0138180 A1 | 7/2004 | Ahmed et al. | |
| 2005/0260262 A1 | 11/2005 | Dansereau et al. | |
| 2007/0218130 A1 | 9/2007 | Ahmed et al. | |

FOREIGN PATENT DOCUMENTS

| | | |
|---|---|---|
| EP | 1 491 199 A1 | 12/2004 |
| WO | WO 93/09785 A1 | 5/1993 |
| WO | WO 94/12200 A1 | 6/1994 |
| WO | WO 95/08331 A1 | 3/1995 |
| WO | WO 95/29679 A1 | 11/1995 |
| WO | WO 98/56360 A2 | 12/1998 |
| WO | WO 99/18972 A1 | 4/1999 |
| WO | WO 00/21540 A1 | 4/2000 |
| WO | WO 00/21541 A1 | 4/2000 |
| WO | WO 00/61111 A1 | 10/2000 |
| WO | WO 01/01991 A1 | 1/2001 |
| WO | WO 01/32185 A1 | 5/2001 |
| WO | WO 01/82903 A1 | 11/2001 |
| WO | WO 01/85176 A1 | 11/2001 |
| WO | WO 2005/030177 A2 | 4/2005 |
| WO | WO 2005/063203 A2 | 7/2005 |
| WO | 2005/079811 | 9/2005 |
| WO | WO 2006/018033 A1 | 2/2006 |
| WO | WO 2006/046100 A1 | 5/2006 |
| WO | 2006/058059 | 6/2006 |
| WO | WO 2006100527 A1 * | 9/2006 |

OTHER PUBLICATIONS

Wet-Granulation Method. Remington's Pharmaceutical Sciences, Gennaro, Ed., Mack Publishing Co., PA, p. 1610-1613 (1985).*
International Search Report for International Application No. PCT/GB2007/003224, mailed Feb. 29, 2008, European Patent Office, The Netherlands.
International Preliminary Report on Patentability for International Application No. PCT/GB2007/003224, mailed Dec. 3, 2008, European Patent Office, Munich, Germany.

* cited by examiner

*Primary Examiner* — Kortney L Klinkel
*Assistant Examiner* — Lisbeth C Robinson
(74) *Attorney, Agent, or Firm* — Florek & Endres PLLC

(57) ABSTRACT

A solid dosage form comprises coated particles of bisphosphonate or a pharmaceutically acceptable analogue or derivative thereof.

12 Claims, No Drawings

SOLID DOSAGE FORM OF COATED BISPHOSPHONATE PARTICLES

The present invention relates to solid dosage forms comprising bisphosphonate, in particular to solid dosage forms which reduce the incidence of gastric irritation.

Bisphosphonates are commonly used in the prophylaxis and treatment of osteoporosis and corticosteroid-induced osteoporosis. They have also been implicated for the treatment of tumour-induced hypercalcaemia. Bisphosphonates are synthetic analogues of natural pyrophosphate that inhibit osteoclast activity and decrease bone turnover and resorption.

Whilst it is known to treat osteoporosis with bisphosphonates, there are a number of gastrointestinal symptoms associated with this class of drug such as abdominal pain, dyspepsia, diarrhea or constipation. Severe gastrointestinal reactions and esophageal reactions such as esophagitis, erosions, and ulceration have been reported. As a consequence, bisphosphonates should not be administered to patients with abnormalities of the esophagus or other factors that might delay esophageal emptying, or those unable to stand, or sit upright for at least 30 minutes (Martindale). Strict instructions are set out for taking these drugs—patients taking alendronate are instructed to take it on an empty stomach before food and to remain sitting upright without eating for at least 30 minutes after taking the drug. Similar instructions, in some cases stricter, apply to other bisphosphonates.

The reason for these instructions is that bisphosphonates can provoke severe esophageal irritation. This can lead to reflux into the esophagus and consequent ulceration, esophagitis, heartburn and retrosternal pain, pain on swallowing and dysphagia. In addition to these side-effects, there is reduced patient compliance with the bisphosphonate treatment, leading to progression of the osteoporosis.

Bisphosphonate treatment is so effective that it is very widely used. Patients have hitherto had to put up with the adverse symptoms associated with bisphosphonate use as there is no alternative treatment that gives such good results.

In addition to the gastric side effects mentioned above, bisphosphonates have relatively low bioavailability. Some bisphosphonates also contain amine groups which can result in incompatibilities with commonly used tablet excipients.

Any steps taken to protect against one of these problems may also exacerbate one of the others. For example, coating a dosage form to aid esophageal transit and lessen the possibility for irritation may lead to reduced bioavailability due to the slower release from the dosage form and the small window of absorption for the compounds. Similarly, seeking to increase disintegration and/or dissolution to increase the opportunity for absorption may in turn lead to a greater incidence of gastric irritation.

General formulations for bisphosphonates have used specific excipients and have been formed using techniques such as direct compression and aqueous granulation which afford simple processing steps, as described in WO94/12200 and WO95/29679.

In order to produce a stable dosage form, formulations have also been developed by paying particular attention to the method of manufacture and choice and amount of excipients, as described, for example, in WO00/21540.

Despite the development of these formulations the bioavailability of the bisphosphonate can still be affected by the presence of food and minerals in the gastrointestinal tract. In a bid to overcome the inherent low bioavailability of the bisphosphonates a number of formulation strategies have been developed. One such strategy, described in WO99/18972, incorporates medium chain triglycerides into the formulation in an attempt to increase the bioavailability. Similarly, incorporation of surfactants and oils has been suggested in WO00/61111 as a suitable method of increasing availability.

Further, as discussed in WO00/21541, concerns over the tendency of bisphosphonates to form complexes with polyvalent metal ions during the formulation process itself have led to the development of specific methods of granulation to ensure uniformity of content.

Another approach, discussed in US2005/0260262, has been to incorporate chelating agents into the formulations to try and ensure a lack of interference from food and beverages.

Conversely, ensuring that the drug is available for absorption and free from any interference from food in the gastrointestinal tract can highlight the undesired side-effects of the bisphosphonates. As discussed above, they have been reported as causing localized irritation when administered orally. A number of strategies have then been developed to overcome this problem.

As discussed in WO93/09785, WO95/08331, WO01/32185, WO01/82903, U.S. Pat. No. 6,676,965 and WO01/01991, the use of enteric coatings and the incorporation of a hydrophobic wax coating have been suggested as methods of ensuring that the active substance does not come into contact with the gastric mucosa.

However, the bisphosphonates also have a relatively low extent of absorption from the gastrointestinal tract and the inclusion of any coating must not interfere unduly with the release and absorption of the drug. The inclusion of a step of coating the dosage form also increases the manufacturing cost since it requires an additional step and additional manufacturing apparatus.

Another method involves the use of specially shaped tablets to reduce the incidence of the problem. Unfortunately, these methods rely upon the use of specialized manufacturing equipment which results in high manufacturing costs and concomitant high unit costs for the tablets produced by the methods.

It is, therefore, an object of the present invention to seek to alleviate problems associated with the known methods of bisphosphonate oral dosage form production.

According to a first aspect of the present invention, there is provided a solid dosage form comprising coated particles of bisphosphonate or a pharmaceutically acceptable analogue or derivative thereof.

The present invention, therefore, relates to a solid dosage form wherein the drug itself, typically as a fine particle, is coated rather than the entire dosage form. This greatly increases the ease of manufacture of dosage forms comprising the drug because standard formulation techniques can be used to produce, for example, tablets comprising the coated drug. There is no need for methods which involve coating the entire tablet, or for specialized tablet presses to be used to produce tablets of peculiar shapes and sizes.

Such a formulation also allows rapid disintegration of the solid dosage form whilst at the same time minimising the gastric irritation produced by the bisphosphonate.

Preferably, the bisphosphonate is selected from risedronate, ibandronate, pamidronate, clodronate, zoledronate, etidronate, tiludronate and alendronate.

In some embodiments, the particles are coated with a water soluble coating. Preferably, the water soluble coating comprises polyethylene glycol, polyvinyl alcohol, hydroxypropylmethylcellulose, hydroxypropylcellulose, povidone, or a pharmaceutically acceptable sugar, more preferably, sorbitol, mannitol, xylitol or maltitol.

In other embodiments, the particles are coated with colloidal silicon dioxide, preferably adhered with polyvinylpyrrolidone.

Such coatings have been found to be particularly effective for allowing rapid release and absorption of the bisphosphonate and minimising the incidence of gastric irritation.

Preferably, the amount of coating is up to about 100% of the uncoated particle weight, further preferably between about 10% and 70% of the uncoated particle weight, more preferably between about 20% and 50% of the uncoated particle weight.

In an embodiment, particles are coated with colloidal silicon dioxide, and it is preferred that the coating is around 20% of the uncoated particle weight. Thus a particle weighing 100 units has a coating weighing 20 units—the coated particle weighs 120 units. In another embodiment, the particles are coated with a pharmaceutically acceptable sugar, and it is preferred that the coating is around 30% of the uncoated particle weight.

Preferably, up to about 75% of the weight of the solid dosage form comprises coated particles, more preferably between about 10% and 50% of the weight of the solid dosage form, further preferably between about 20% and 40% of the weight of the solid dosage form.

In preferred embodiments the dosage form itself is uncoated.

Preferably, the particles are coated with a coating which does not substantially affect absorption of the bisphosphonate. Preferably, the coating is pharmaceutically compatible with the bisphosphonate coated.

Conveniently, the solid dosage form further comprises a disintegrant. Preferably, up to about 85% of the weight of the solid dosage form comprises disintegrant, more preferably between about 30% and 80% disintegrant.

Preferably, the disintegrant is selected from croscarmellose cellulose, crospovidone, microcrystalline cellulose, croscarmellose sodium and sodium starch glycolate.

Preferably, the solid dosage form is formulated as a tablet. Hence, a particularly preferred embodiment of the invention is an uncoated tablet comprising 20 to 40% by weight coated particles and 30 to 80% by weight disintegrant. Alternatively, the solid dosage form is formulated as a capsule.

In a further embodiment, the solid dosage form additionally comprises other active ingredients, vitamins and mineral supplements, or a mixture thereof.

According to another aspect of the present invention, there is provided a method for formulating a solid dosage form, the method comprising:—
(i) coating particles of bisphosphonate or a pharmaceutically acceptable analogue or derivative thereof;
(ii) mixing the coated particles with one or more excipients; and
(iii) forming the coated particles and one or more excipients into a solid dosage form.

Preferably, the bisphosphonate is selected from risedronate, ibandronate, pamidronate, clodronate, zoledronate, etidronate, tiludronate and alendronate.

In one embodiment, the particles are coated with a water soluble coating, more preferably polyethylene glycol, polyvinyl alcohol, hydroxypropylmethylcellulose, hydroxypropylcellulose, povidone, or a pharmaceutically acceptable sugar, further preferably sorbitol, mannitol, xylitol or maltitol.

In another embodiment, the particles are coated with colloidal silicon dioxide, preferably adhered with polyvinylpyrrolidone.

Preferably, the particles are coated with up to about 100% of their uncoated weight by coating, further preferably between about 10% and 70% of their uncoated weight, more preferably between about 20% and 50% of their uncoated weight.

If the particles are coated with colloidal silicon dioxide, then it is preferred that the particles are coated with around 20% of their uncoated weight by coating. If the particles are coated with a pharmaceutically acceptable sugar, then it is preferred that the particles are coated with around 30% of their uncoated weight by coating.

Preferably, the dosage form resulting from the method comprises up to about 75% by weight of coated particles, more preferably between about 10% and 50% by weight, further preferably, between about 20% and 40% by weight.

In preferred embodiments, the particles are coated with a coating which does not substantially affect absorption of the bisphosphonate.

Preferably, one or more excipients comprise a disintegrant.

Preferably, the dosage form resulting from the method comprises up to about 85% by weight disintegrant, more preferably between about 30% and 80% disintegrant.

Preferably, the disintegrant is selected from croscarmellose cellulose, crospovidone, microcrystalline cellulose, croscarmellose sodium and sodium starch glycolate.

In preferred embodiments, step (iii) comprises compressing the coated particles and one or more excipients into a tablet. Alternatively, step (iii) comprises encapsulating the coated particles and one or more excipients into a capsule.

In one embodiment, the particles of bisphosphonate or a pharmaceutically acceptable analogue or derivative thereof are coated by spraying a coating thereon.

In another embodiment, the particles of bisphosphonate or a pharmaceutically acceptable analogue or derivative thereof are coated by being mixed with a coating solution or suspension. The particles of bisphosphonate or a pharmaceutically acceptable analogue or derivative thereof are preferably mixed with the coating solution or suspension to form a wet mass. The wet mass is then preferably dried.

Preferably, the methods of the present invention do not involve a step of coating the solid dosage form.

After coating of the particles of bisphosphonate, it is optional to mill the coated particles. In embodiments of the invention, the coated particles are milled in the presence of a pharmaceutically acceptable excipient, prior to being mixed with other excipients and tablet components. Hence a method of the invention comprises:—
(i) coating particles of bisphosphonate or a pharmaceutically acceptable analogue or derivative thereof;
(ii) adding a pharmaceutically acceptable excipient to the coated particles to obtain a combination of excipient and coated particles;
(iii) milling the combination of (ii);
(iv) mixing the combination with one or more excipients; and
(v) forming the coated particles and one or more excipients into a solid dosage form.

It has been found that the milling step is facilitated by the excipient, giving improved processing during tablet manufacture.

The excipient used in step (ii) may be the same as one of the one or more excipients of (iv), the resulting formulation then containing, say, just one major excipient. The excipient of (ii) can be selected from cellulose, lactose, starch and calcium phosphate. In examples below, the excipient of (ii) is microcrystalline cellulose.

The method may comprise forming the coated particles and excipient(s) into a tablet or encapsulating the particles and excipient(s) into a capsule.

The processes required to produce formulations of the present invention involve fewer steps than conventional film coating processes and use less expensive excipients.

According to another aspect of the present invention, there is provided a solid dosage form for treating osteoporosis—generally in a human.

Also provided by the present invention is a method for treating osteoporosis, the method comprising administering to a patient suffering from osteoporosis an effective amount of a solid dosage form as described above.

Further provided by the present invention is a method for the prevention of osteoporosis, the method comprising administering to a patient having the potential to suffer from osteoporosis an effective amount of a solid dosage form as described above.

The present invention provides in specific embodiments a formulation retaining all the properties and advantages of known formulations, whilst still reducing the incidence of esophageal irritation and leaving the bioavailability of the drug substantially unaffected.

The particles can be coated with polyethylene glycol, preferably by dissolving the polyethylene glycol in ethanol and spray granulating it onto the particles.

The particles can be coated with sorbitol, preferably by dissolving the sorbitol in water or an ethanol/water mixture, depositing the solution onto the particles by means of known granulation equipment and then drying in a fluid bed dryer. The method may involve a two stage process (each depositing approximately half of the sugar) to deposit a total of 30% by weight of sugar to particles onto the particles.

After drying and sizing (e.g. by milling or sieving), the coated particles are preferably added to normal direct compression excipients, mixed and compressed into tablets.

The particles can be coated with colloidal silicon dioxide by dissolving povidone in ethanol (or ethanol/water) and then adding colloidal silicon dioxide to form a 'slurry' which is deposited/granulated onto the particles and dried. Alternatively, the particles are mixed with colloidal silicon dioxide in a high shear mixer and the silicon dioxide then adhered to the particles by granulating with povidone dissolved in ethanol and/or water. After drying and sizing (by milling or sieving), the coated particles are preferably added to normal direct compression excipients, mixed and compressed into tablets.

Embodiments of the present invention will now be described with reference to the following examples.

EXAMPLE 1

A tablet containing ibandronate coated with sorbitol was formulated as follows:—

38 g sorbitol was dissolved in an ethanol/water mix containing 31 ml absolute ethanol and 20 ml purified water. The solution was mixed thoroughly until the sorbitol was in solution, the solution being heated to around 37° C. to aid dissolution of the sorbitol. The solution was added to 253.1 g ibandronate sodium monohydrate and the mixture granulated in a high shear granulator in a 1 l bowl. The granulate was then dried at around 35° C. in a fluid bed dryer for between 60 and 90 minutes. The dried granulate was sieved through a number 30 mesh screen.

A further 38 g sorbitol was dissolved in an ethanol/water mix containing 31 ml absolute ethanol and 20 ml purified water. The solution was mixed thoroughly until the sorbitol was in solution. (If necessary, the solution was heated to around 37° C. to aid dissolution of the sorbitol.) The solution was then added to the dried and sieved granulate, the mixture was granulated in a high shear granulator and the granulate dried at around 35° C. in a fluid bed dryer for between 60 and 90 minutes. The dried granulate was then sieved through a number 30 mesh screen.

462.9 g microcrystalline cellulose, 8.1 g colloidal silicon dioxide and 25.5 g croscarmellose sodium were pre-screened through a number 20 mesh screen, added to the dried and sieved granulate and then blended in a 5 l V-Tumble Blender for 20 minutes. 16.2 g sodium stearyl fumarate was pre-screened through a number 40 mesh screen, added to the blended mixture, and the mixture blended for a further 10 minutes.

The blended mixture was then compressed into tablets with a target weight of 200 mg on a Korsch XL100 Tablet Press.

Thus, tablets having the following composition were obtained:—

| | |
|---|---|
| Ibandronate sodium monohydrate | 56.25 mg |
| Sorbitol | 16.9 mg |
| Microcrystalline cellulose | 114.55 mg |
| Colloidal silicon dioxide | 2.0 mg |
| Croscarmellose sodium | 6.3 mg |
| Sodium stearyl fumarate | 4.0 mg |

EXAMPLE 2

A tablet containing ibandronate coated with colloidal silicon dioxide was formulated as follows:—

2.3 g povidone was dissolved in 100 ml absolute ethanol and mixed thoroughly. 253.1 g ibandronate sodium monohydrate and 50.6 g colloidal silicon dioxide were mixed together for 5 minutes in a high shear mixer and then the povidone/ethanol mix was added and granulated in a high shear granulator in a 3 l bowl.

Alternatively, the colloidal silicon dioxide was added to the povidone/ethanol mix to form a slurry which was then deposited or granulated onto the ibandronate sodium monohydrate.

The granulate was then dried at around 35° C. in a fluid bed dryer for between 60 and 90 minutes. The dried granulate was sieved through a number 30 mesh screen.

462.4 g microcrystalline cellulose, 7.5 g colloidal silicon dioxide and 25.7 g croscarmellose sodium were pre-screened through a number 14 mesh screen, added to the dried and sieved granulate and then blended in a 5 l V-Tumble Blender for 20 minutes. 15.5 g sodium stearyl fumarate was pre-screened through a number 40 mesh screen, added to the blended mixture, and the mixture blended for a further 10 minutes.

The blended mixture was then compressed into tablets with a target weight of 200 mg on a Korsch XL100 Tablet Press.

Thus, tablets having the following composition were obtained:—

| | |
|---|---|
| Ibandronate sodium monohydrate | 56.25 mg |
| Colloidal silicon dioxide (coating) | 11.25 mg |
| Povidone | 0.50 mg |
| Microcrystalline cellulose | 119.35 mg |
| Colloidal silicon dioxide (extra-granular excipient) | 2.0 mg |
| Croscarmellose sodium | 6.65 mg |
| Sodium stearyl fumarate | 4.0 mg |

EXAMPLE 3

A tablet containing risedronate coated with sorbitol was formulated as follows:—

44.8 g sorbitol was dissolved in an ethanol/water mix containing 39 ml absolute ethanol and 26 ml purified water. The solution was mixed thoroughly until the sorbitol was in solution, the solution being heated to around 37° C. to aid dissolution of the sorbitol. The solution was added to 298.2 g risedronate sodium and the mixture granulated in a high shear granulator in a 1 l bowl. The granulate was then dried at around 35° C. in a fluid bed dryer for around 60 minutes. The dried granulate was sieved through a number 30 mesh screen.

A further 44.8 g sorbitol was dissolved in an ethanol/water mix containing 39 ml absolute ethanol and 26 ml purified water. The solution was mixed thoroughly until the sorbitol was in solution. (If necessary, the solution was heated to around 37° C. to aid dissolution of the sorbitol.) The solution was then added to the dried and sieved granulate, the mixture was granulated in a high shear granulator and the granulate dried at around 35° C. in a fluid bed dryer for about 60 minutes. The dried granulate was then sieved through a number 30 mesh screen.

868.6 g microcrystalline cellulose, 9.9 g colloidal silicon dioxide and 31.1 g croscarmellose sodium were pre-screened through a number 14 mesh screen, added to the dried and sieved granulate and then blended in a 5 l V-Tumble Blender for 20 minutes. 19.7 g sodium stearyl fumarate was pre-screened through a number 40 mesh screen, added to the blended mixture, and the mixture blended for a further 10 minutes.

The blended mixture was then compressed into tablets with a target weight of 240 mg on a Korsch XL100 Tablet Press.

Thus, tablets having the following composition were obtained:—

| | |
|---|---|
| Risedronate sodium | 39.76 mg |
| Sorbitol | 11.94 mg |
| Microcrystalline cellulose | 176.0 mg |
| Colloidal silicon dioxide | 2.0 mg |
| Croscarmellose sodium | 6.3 mg |
| Sodium stearyl fumarate | 4.0 mg |

EXAMPLE 4

A tablet containing risedronate coated with colloidal silicon dioxide was formulated as follows:—

3.75 g povidone was dissolved in 100 ml absolute ethanol and mixed thoroughly. 298.2 g risedronate sodium and 59.63 g colloidal silicon dioxide were mixed together for 5 minutes in a high shear mixer and then the povidone/ethanol mix was added and granulated in a high shear granulator in a 3 l bowl.

Alternatively, the colloidal silicon dioxide was added to the povidone/ethanol mix to form a slurry which was then deposited or granulated onto the risedronate sodium.

The granulate was then dried at around 35° C. in a fluid bed dryer for about 60 minutes. The dried granulate was sieved through a number 30 mesh screen.

1032.5 g microcrystalline cellulose, 11.5 g colloidal silicon dioxide and 36.3 g croscarmellose sodium were pre-screened through a number 14 mesh screen, added to the dried and sieved granulate and then blended in a 10 l V-Tumble Blender for 20 minutes. 23.0 g sodium stearyl fumarate was pre-screened through a number 40 mesh screen, added to the blended mixture, and the mixture blended for a further 10 minutes.

The blended mixture was then compressed into tablets with a target weight of 240 mg on a Korsch XL100 Tablet Press.

Thus, tablets having the following composition were obtained:—

| | |
|---|---|
| Risedronate sodium | 39.76 mg |
| Colloidal silicon dioxide (coating) | 7.95 mg |
| Povidone | 0.50 mg |
| Microcrystalline cellulose | 179.49 mg |
| Colloidal silicon dioxide (extra-granular excipient) | 2.0 mg |
| Croscarmellose sodium | 6.3 mg |
| Sodium stearyl fumarate | 4.0 mg |

EXAMPLE 5

A tablet containing risedronate coated with polyethylene glycol was formulated by dissolving polyethylene glycol in ethanol and then spray granulating the mixture onto risedronate sodium. The coated risedronate sodium was then dried and sieved to form a granulate.

Microcrystalline cellulose, colloidal silicon dioxide and croscarmellose sodium were pre-screened through a number 14 mesh screen, added to the dried and sieved granulate and then blended in a 10 l V-Tumble Blender for 20 minutes. Sodium stearyl fumarate was pre-screened through a number 40 mesh screen, added to the blended mixture, and the mixture blended for a further 10 minutes.

The blended mixture was then compressed into tablets on a Korsch XL100 Tablet Press.

EXAMPLES 6-9

Further tablets were made in accordance with the invention using the active risedronate which was coated with sorbitol then incorporated into a tablet.

| | Example | | | | |
|---|---|---|---|---|---|
| | 6<br>5 mg | 7<br>30 mg | 8<br>35 mg | 9<br>75 mg | Notes |
| Risedronate Sodium (Theoretical) | 5.00 | 30.00 | 35.00 | 75.00 | Measured as mg of active |
| Sorbitol Crystalline | 9.60 | 9.60 | 9.60 | 19.20 | 3% Sorbitol in solution to coat |
| Microcrystalline Cellulose 102 | 50.00 | 25.00 | 20.00 | 35.00 | MCC to the same granulation weight. |
| Water | q.s. | q.s. | q.s. | q.s. | |
| Microcrystalline Cellulose 102 | 126.00 | 151.00 | 156.00 | 317.00 | Total MCC = 176.0 mg/tab (or 55%) |
| Sorbitol Crystalline | 113.40 | 88.40 | 83.40 | 161.80 | Total Sorbitol = 128 − (active) mg/tab |
| Colloidal Silicon Dioxide | 3.20 | 3.20 | 3.20 | 6.40 | 1% SiO2 |
| Croscarmellose Sodium | 6.40 | 6.40 | 6.40 | 12.80 | 2% Croscarmellose Na |
| Sodium Stearyl Fumarate | 6.40 | 6.40 | 6.40 | 12.80 | 2% SSF |
| Total Tablet Weight, mg: | 320.00 | 320.00 | 320.00 | 640.00 | Active and sorbitol only adjustments <10% |

These examples included a carrier excipient, microcrystalline cellulose, already present as filler and disintegrant, found to improve milling of material after coating.

Although the examples describe how to formulate a tablet according to the present invention, it will be understood that a person skilled in the art will be able to formulate a capsule according to the present invention by, for example, encapsulating the blended mixture into capsules instead of compressing the blended mixture into tablets.

The present invention thus provides a solid dosage form of a bisphosphonate.

The invention claimed is:

1. A method for formulating a solid dosage form, comprising:
    (i) combining particles of bisphosphonate with a coating solution or suspension consisting essentially of a coating and a solvent, wherein the coating contains a pharmaceutically acceptable, water soluble sugar and the amount of coating is from 10% to 70% by weight of the uncoated particles;
    (ii) drying the solution or suspension to form coated particles of bisphosphonate;
    (iii) mixing the coated particles of (ii) with one or more excipients; and
    (iv) forming the coated particles and one or more excipients into a solid dosage form, wherein the solid dosage form is formulated as a tablet and the tablet is not coated and comprises 20% to 40% by weight coated particles and 30% to 80% by weight disintegrant.

2. The method of claim 1, wherein the bisphosphonate is selected from the group consisting of risedronate, ibandronate, pamidronate, clodronate, zoledronate, etidronate, tiludronate, and alendronate.

3. The method of claim 1, wherein the pharmaceutically acceptable water soluble sugar is selected from the group consisting of sorbitol, mannitol, xylitol, and maltitol.

4. The method of claim 1, wherein the amount of coating in (i) is from 20% to 50% by weight of the uncoated particles.

5. The method of claim 4, wherein the amount of coating in (i) is about 30% by weight of the uncoated particles.

6. The method of claim 1 wherein the disintegrant is selected from the group consisting of croscarmellose cellulose, crospovidone, microcrystalline cellulose, croscarmellose sodium and sodium starch glycolate.

7. A method of formulating a solid dosage form, comprising:
    (i) forming a colloidal silicon dioxide coated bisphosphonate particle by depositing to a bisphosphonate particle, or granulating with a bisphosphonate particle, a composition comprising colloidal silicon dioxide and a water soluble binder, wherein the amount of colloidal silicon dioxide deposited to or granulated with the particles is from 10% to 70% by weight of the particles prior to the depositing or granulating;
    (ii) mixing the resultant colloidal silicon dioxide coated bisphosphonate particles of (i) with one or more excipients; and
    (iii) forming the mixture of colloidal silicon dioxide coated bisphosphonate particles and one or more excipients into a solid dosage form, wherein the solid dosage form is formulated as a tablet.

8. The method of claim 7, wherein the bisphosphonate is selected from the group consisting of risedronate, ibandronte, pamidronate, clodronate, zoledronate, etidronate, tiludronate, and alendronate.

9. The method of claim 7, wherein the colloidal silicon dioxide is deposited to, or granulated with, the particles in an amount about 20% to about 50% by weight of the particles prior to the depositing or granulating.

10. The method of claim 7, wherein the solid dosage form is not coated.

11. The method of claim 7 wherein the water soluble binder is selected from the group consisting of polyethylene glycol, polyvinyl alcohol, hydroxypropylmethylcellulose, hydroxypropylcellulose, povidone, sorbitol, mannitol, xylitol and maltitol.

12. The method of claim 11 wherein the water soluble binder is povidone.

* * * * *